US00PP13971P29

(12) United States Plant Patent
van Delft

(10) Patent No.: US PP13,971 P2
(45) Date of Patent: Jul. 15, 2003

(54) OXALIS PLANT NAMED 'AMARANTHA'

(75) Inventor: Luite Cornelis Johannes van Delft, Noordwykerhout (NL)

(73) Assignee: Future Plants V.O.F., Lisserbroek (NL)

( * ) Notice: Subject to any disclaimer, the term of this patent is extended or adjusted under 35 U.S.C. 154(b) by 0 days.

(21) Appl. No.: 10/139,962

(22) Filed: May 6, 2002

(51) Int. Cl.[7] ..... A01H 5/00
(52) U.S. Cl. ..... Plt./263
(58) Field of Search ..... Plt./263

(56) References Cited

PUBLICATIONS

"*Oxalis bowiei*" Http://www.plantcare.com/catalog/tep-Plan...E+%27O%25%27+&TotalOffset=80&T0talNum=83.*

"Perennials M–O" http://www.sugarcreekgardens.com/Perennials%20M–O.htm.*

UPOV ROM GTITM Computer Database, GTI JOUVE Retrieval Software 2002/02, citations for 'Amarantha'.*

* cited by examiner

*Primary Examiner*—Bruce R. Campell
*Assistant Examiner*—W C Haas
(74) *Attorney, Agent, or Firm*—C. A. Whealy

(57) ABSTRACT

A distinct cultivar of Oxalis plant named 'Amarantha', characterized by its outwardly spreading to procumbent plant habit; large trifoliate leaves; freely flowering habit; and large red purple-colored flowers.

1 Drawing Sheet

BOTANICAL CLASSIFICATION/CULTIVAR DESIGNATION

*Oxalis bowiei* cultivar Amarantha.

BACKGROUND OF THE INVENTION

The present Invention relates to a new and distinct cultivar of Oxalis plant, botanically known as *Oxalis bowiei,* and hereinafter referred to by the cultivar name Amarantha.

The new Oxalis originated from a chance cross-pollination of two unidentified selections of *Qxalis bowiei,* not patented. The new Oxalis was discovered by the Inventor in 1998 in Noordwykerhout, The Netherlands. Plants of the new Oxalis differed primarily from plants of the unidentified parental selections in flower size and flower color.

Asexual reproduction of the new cultivar by bulbs in Noordwykerhout, The Netherlands since 1998, has shown that the unique features of this new Oxalis are stable and reproduced true to type in successive generations.

SUMMARY OF THE INVENTION

Plants of the cultivar Amarantha have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'Amarantha'. These characteristics in combination distinguish 'Amarantha' as a new and distinct cultivar:

1. Outwardly spreading to procumbent plant habit.
2. Large trifoliate leaves.
3. Freely flowering habit.
4. Large red purple-colored flowers.

Plants of the new Oxalis can be compared to plants of an unidentified selection of *Oxalis bowiei,* not patented. In side-by-side comparisons conducted in Noordwykerhout, The Netherlands, plants of the new Oxalis differed from the unidentified selection of *Oxalis bowiei* in the following characteristics:

1. Plants of the new Oxalis were larger than plants of the unidentified selection of *Oxalis bowiei.*
2. Plants of the new Oxalis had larger flowers plants of the unidentified selection of *Oxalis bowiei.*
3. Plants of the new Oxalis had more intense red purple-colored flowers than plants of the unidentified selection of *Oxalis bowiei.*

BRIEF DESCRIPTION OF THE PHOTOGRAPHS

The accompanying colored photographs illustrate the overall appearance of the new Oxalis, showing the colors as true as it is reasonably possible to obtain in colored reproductions of this type. Colors in the photographs may differ slightly from the color values cited in the detailed botanical description which accurately describe the colors of the new Oxalis.

The photograph at the top of the sheet comprises a side perspective view of a typical flowering plant of 'Amarantha'.

The photograph at the bottom of the sheet comprises a close-up view of typical flowers of 'Amarantha'.

DETAILED BOTANICAL DESCRIPTION

In the following description, color references are made to The Royal Horticultural Society Colour Chart, 2001 Edition, except where general terms of ordinary dictionary significance are used. Plants used for the following description were about three months from planting and grown under outdoor field conditions which closely approximate commercial production conditions in Noordwykerhout, The Netherlands. The photograph and the description information were taken during the summer, 2001.

Botanical classification: *Oxalis bowiei* cultivar Amarantha.

Parentage: Cross-pollination of two unidentified selections of *Oxalis bowiei,* not patented.

Propagation:

*Type.*—By bulbs.

*Root description.*—Fine; light brown in color.

Plant description:

*Form.*—Perennial flowering plant; outwardly spreading to procumbent; freely basal branching with leaves and flowering scapes arising from the plant base; moderately vigorous to vigorous growth habit.

*Plant height.*—About 25 cm.

*Plant diameter.*—About 30 cm.

*Foliage description.*—Arrangement: Alternate, compound, tri-foliate. Leaflet: About 5 cm. Leaflet width: About 5.3 cm. Leaflet shape: Obcordate. Leaflet apex: Retuse. Leaflet base: Attenuate. Leaflet margin: Entire. Leaflet texture, upper surface: Smooth, glabrous. Leaflet texture, lower surface: Pubescent. Leaflet venation pattern: Pinnate. Petiole: Length: About 10 cm. Diameter: About 2.5 mm. Texture: Pubescent. Leaflet color: Young foliage, upper surface: 143B. Young foliage, lower surface: 143C. Fully expanded foliage, upper surface: 137A. Fully expanded foliage, lower surface: 138B. Venation, upper surface: 137A. Venation, lower surface: 138B to 138C. Petiole: 143A to 143B.

Flower description:

*Appearance.*—Single rotate flowers with five petals fused at the base. Flowers arranged on scapose umbellate cymes; typically about ten open flowers and flower buds per cyme. Flowers not persistent. Flowers face upright to outward.

*Natural flowering season.*—Plants flower continuously during the summer in Noordwykerhout, The Netherlands.

*Fragrance.*—None detected.

*Flower longevity.*—About five days.

*Flower diameter.*—About 3.8 cm.

*Flower depth* (*height*).—About 1.8 cm.

*Flower bud.*—Length: About 1.7 cm. Diameter: About 5 mm. Shape: Ovoid. Color: 67B.

*Petals.*—Quantity per flower: Five. Arrangement: Rotate; fused at base. Length: About 2.4 cm. Width: About 1.8 cm. Shape: Roughly spatulate. Apex: Broadly obtuse; slightly undulate. Base: Fused. Margin: Entire. Texture, upper and lower surfaces: Smooth, glabrous. Color: When opening, upper surface: 66B. When opening, lower surface: 67C to 68A. Fully opened, upper surface: 67B; color becoming closer to 70A with subsequent development. Fully opened, lower surface: 68A. Throat: Close to 9A.

*Sepals.*—Quantity per flower: Five. Arrangement: Rotate; campanulate. Calyx length: About 2.6 cm. Calyx diameter: About 2.7 cm. Shape: Lanceolate. Apex: Acute. Base: Fused. Margin: Entire. Texture, upper and lower surfaces: Pubescent. Color, upper surface: 137B. Color, lower surface: 137C to 138A.

*Scape.*—Number per plant: About five. Length: About 30 cm. Diameter: About 3.5 mm. Angle: About 60 to 90° from vertical. Strength: Moderately strong; flexible. Texture: Pubescent. Color: 144B.

*Pedicels.*—Length: About 2.4 cm. Diameter: About 1.2 mm. Angle: About 90 to 180° from vertical. Strength: Moderately strong. Color: 144B.

*Bracts.*—Arrangement: One bract at base of pedicel. Length: About 7 mm. Width: About 1 mm. Shape: Linear. Apex: Acute. Texture, upper and lower surfaces: Smooth. Color, upper and lower surfaces: 143A to 143B.

*Reproductive organs.*—Stamens: Quantity per flower: About ten. Anther shape: Oblong; dorsifixed. Anther length: About 1 mm. Anther color: 13A. Pollen amount: Scarce. Pollen color: Close to 13A. Pistils: Quantity per flower: About ten. Pistil length: About 4 to 7 mm. Style length: About 4 to 7 mm. Style color: 150A. Stigma shape: Terete. Stigma color: 150A. Ovary color: 142A.

*Seed/fruit.*—Seed and fruit production have not been observed.

Disease/pest resistance: Plants of the new Oxalis have not been noted to be resistant to pathogens or pests common to Oxalis.

Temperature tolerance: Plants of the new Oxalis are tolerant to temperatures from about 15 to 35° C.

It is claimed:

1. A new and distinct cultivar of Oxalis plant named 'Amarantha', as illustrated and described.

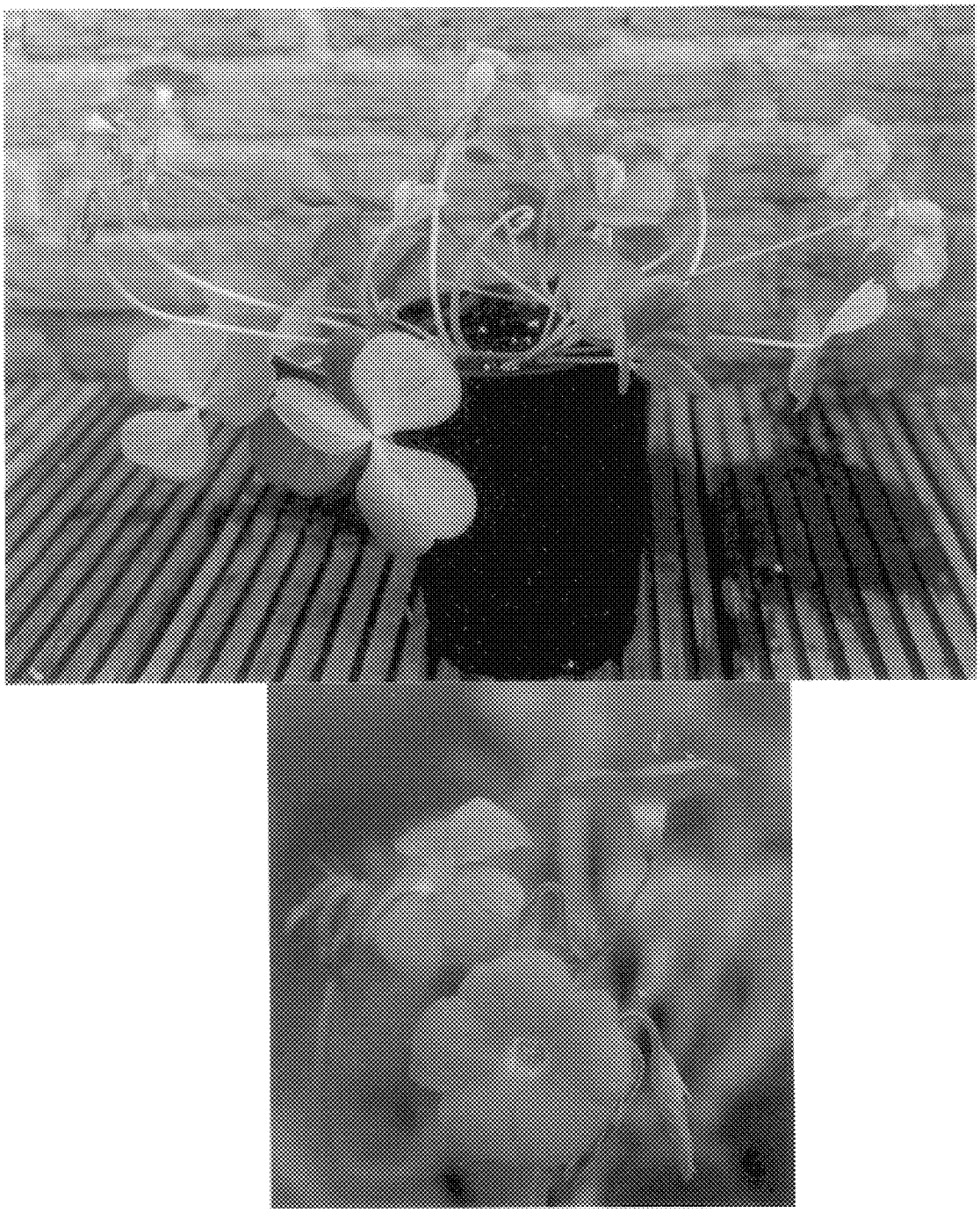

* * * * *